United States Patent [19]
Didillon et al.

[11] Patent Number: 5,235,106
[45] Date of Patent: Aug. 10, 1993

[54] CATALYTIC REDUCTION OF SUBSTITUTED OR UNSUBSTITUTED NITROAROMATIC COMPOUND TO CORRESPONDING AMINOAROMATIC COMPOUNDS

[75] Inventors: Blaise Didillon, Lyons; Fabienne Le Peltier, Rueil Malmaison; Jean-Pierre Candy, Caluire; Patrick Sarrazin, Rueil Malmaison; Jean-Paul Boitiaux, Poissy; Jean-Marie Basset, Villeurbanne, all of France

[73] Assignee: Institut Francais Du Petrole, Rueil Malmaison, France

[21] Appl. No.: 817,559

[22] Filed: Jan. 7, 1992

[30] Foreign Application Priority Data

Jan. 7, 1991 [FR] France ............... 91 00132

[51] Int. Cl.$^5$ ............................ C07C 209/36
[52] U.S. Cl. ..................... 564/417; 564/418; 564/422
[58] Field of Search ............ 564/418, 417, 422; 502/154

[56] References Cited

U.S. PATENT DOCUMENTS

| | | | |
|---|---|---|---|
| 3,666,813 | 5/1972 | Hindin et al. | 260/580 |
| 4,265,834 | 5/1981 | Birkenstock et al. | 564/421 |
| 4,316,500 | 11/1982 | Mathe et al. | 252/430 |
| 4,760,187 | 7/1988 | Kosak | 564/417 |

OTHER PUBLICATIONS

CA 98:106948d Dec. 1983.
CA 109:5958x Jun. 1988.
CA 96:142436c Mar. 1982.
CA 89:6092r Apr. 1978.
*The American Heritage Dictionary*, Second College Edition, p. 1140, 1991.
*Grant & Hackh's Chemical Dictionary*, Fifth Edition, p. 531, McGraw-Hill. 1987.

*Primary Examiner*—Richard L. Raymond
*Assistant Examiner*—Brian M. Burn
*Attorney, Agent, or Firm*—Millen, White, Zelano & Branigan

[57] ABSTRACT

The invention concerns the production of a substituted or unsubstituted aniline by selective hydrogenation of the corresponding nitroaromatic compound. It is characterized by the use of a catalyst based on a metal selected from rhodium and ruthenium and based on a metal selected from the group comprising tin, germanium and lead.

12 Claims, No Drawings

CATALYTIC REDUCTION OF SUBSTITUTED OR UNSUBSTITUTED NITROAROMATIC COMPOUND TO CORRESPONDING AMINOAROMATIC COMPOUNDS

The invention concerns a method of producing substituted or unsubstituted aniline by hydrogenating the corresponding nitroaromatic compound.

The nitroaromatic compounds are of the following general formulae (I) or (II):

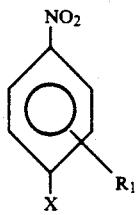
(I)

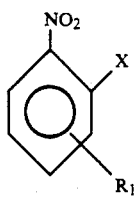
(II)

where X is a halogen and R$_1$ is hydrogen or a substituent of the aromatic ring selected from: alkyls, halogens, alkenyls, sulphoxy, nitro, nitroso, amines, hydroxyl, ethoxys and acetoxys.

Selective hydrogenation of the nitro function or functions by the aromatic ring in the presence of hydrogen leads to the formation of amines of the following empirical formula (III) or (IV):

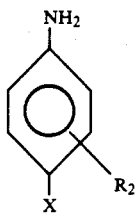
(III)

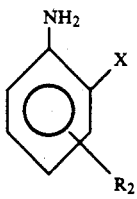
(IV)

where X is a halogen and R$_2$ is hydrogen or a substituent of the aromatic ring selected from: alkyls, halogens, alkenyls, sulphoxy, amines, hydroxyl, ethoxys and acetoxys.

These products are used in many industrial sectors, and special mention ma be made of dye chemistry.

One of the disadvantages encountered in carrying out the reaction is that some of the reaction products undergo hydrogenolysis of the carbon - halogen X bonds, leading to the following by-products of formula (V) or (VI):

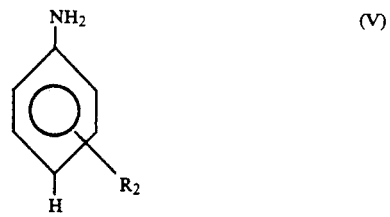
(V)

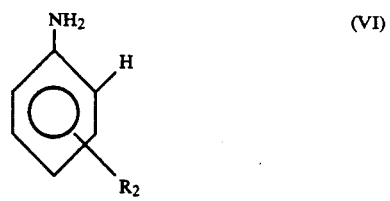
(VI)

where R is hydrogen or a substituent of the aromatic ring selected from: alkyls, halogens, alkenyls, sulphoxy, amines, hydroxyl, ethoxys and acetoxys.

In addition, whether or not there is a substituent other than the nitro group on the aromatic ring, it has been found that decomposition of partially reduced reaction intermediates of the hydroxylamine, azoxy, azo or hydrazo type leads to the formation of heavy by-products (KIRK-OTHMER Encycl. chem. Technol. 3rd Ed. Vol.2, 355), which reduce the total yield of the reaction and cause excessive catalyst consumption.

High conversion levels, and if possible total conversion, with the best possible selectivity, are thus difficult to obtain for this rearrangement.

Group VIII metals are known to catalyse reduction of nitroaromatic compounds under hydrogen pressure. They operate advantageously in liquid phase, that is to say, in the presence of a solvent, but worthwhile selectivities can only be obtained by adding materials. Thus selective hydrogenation of nitrochlorinated aromatic compounds has been described, in the presence of a sulphurised platinum catalyst supported on charcoal (DE-B-1.959.578) and on other catalysts based on sulphurised Group VIII metals (US-A-3.350.450). These sulphurised metals are generally relatively inactive, and it is sometimes preferred to add the selectivity-producing agent to the reaction medium. Thus the use of inhibitors such as triphenylphosphite (US-A-3.474.144) or morpholine (US-A-3.145.231) in the presence of platinum-based catalyst enables dehalogenation of the reaction products to be considerably limited. More recently patent EP-B-325.892 claims to obtain high selectivities, using formamidine salts to inhibit the dehalogenation reaction, in the presence of catalyst based on Raney nickel.

Conversion of these nitroaromatic compounds is described in a number of publications. The use of nickel boride as catalyst instead of Raney nickel appears to limit the reaction intermediates responsible for forming heavy by-products (Ind. Eng. Chem. Prod. Res. Dev., 21, 279–281 1982). The same catalyst in the presence of formamidine acetate in methanol enables 99.4% selectivity for 1-chloro 2-nitrobenzene to be obtained (Heterogeneous catalysis and fine chemicals, 2nd International Symposium, Guisnet et al, Elsevier to be published).

In the present invention it has been found that substituted or unsubstituted nitroaromatic compounds can be hydrogenated very selectively to corresponding aminoaromatic compounds without diminishing the activity of the basic metal; the activity of the metal may in fact be promoted, even if there is no additive in the reaction mixture. The operation takes place in a continuous or discontinuous reactor in the presence of hydrogen, at a total pressure generally of 10 to 100 bars (1–10 megapascal) and preferably 20 to 80 bars (2–8 megapascal), though there is no disadvantage in operating at pressures up to e.g. 300 bars (30 megapascal). The temperature is generally from 0° to 100° C., preferably 30° to 80° C. and at least one supported metal catalyst is present (heterogeneous catalysis). The catalyst contains a) at least one Group VIII metal selected from rhodium and ruthenium (better than the other Group VIII metals), the weight percentage relative to the total mass of catalyst preferably being selected from 0.1 to 10% expressed as metal, and more particularly from 0.5 to 5%, and b) at least one additional metallic element selected from Group IVA comprising tin, germanium and lead, the weight percentage preferably being selected from 0.01 to 10% expressed as metal, and more particularly 0.1 to 5%.

The molar ratio of Group IV metallic element to Group VIII metal is advantageously from 0.8 to 3:1 and preferably from 0.9 to 2.6:1. In some cases it is advantageous to use two or even three of the above-mentioned Group IVA metals at the same time. The carrier may be selected from the group comprising silica, the various types of alumina, silica-aluminas, aluminates of the elements in Groups IA, IIA or IIB of the Periodic Table, such as aluminates of Ca, Mg, Ba, Zn, Na, K or Cd and mixed aluminates, and charcoal; it may preferably be selected from the group comprising silica, aluminates of alkali metals and/or alkaline earth metals and/or zinc and/or cadmium, and mixed aluminates.

The catalyst may be prepared by various procedures for impregnating the carrier. The impregnating operation may, for example, comprise putting the preformed carrier into contact with an aqueous or organic solution of a compound of the selected metal or metals, the volume of solution preferably being in excess of or equal to the retention volume of the carrier. When the carrier and solution have been left in contact for some hours the impregnated carrier is filtered, washed with distilled water, dried and calcined in air, generally at from 110° to 600° C. and preferably from 110° to 500° C. When the catalyst has been used it is reduced in hydrogen, usually at from 50° to 600° C. and preferably from 90° to 500° C; this may be done immediately after calcination, or later by the user.

The element from the group comprising tin, germanium and lead may be introduced in aqueous or hydrocarbon solution, according to the type of precursor used.

The catalyst is preferably obtained by impregnating the carrier with an aqueous or organic solution of at least one compound of the Group VIII metal, the volume of solution preferably being in excess of or equal to the retention volume of the carrier. The impregnated carrier is then filtered, possibly washed with distilled water, then dried and calcined in air, normally at from about 110° to about 600° C. and preferably from about 110° to about 500° C, then reduced in hydrogen at a temperature normally from about 50° to about 600°C. and preferably from about 80° to about 500°C. The product obtained is then impregnated with an aqueous or organic solution of a tin, germanium and/or lead compound; it is particularly advantageous to use a solution of at least one hydrocarbyl germanium, one hydrocarbyl tin or one hydrocarbyl lead in a saturated hydrocarbon, with the technology described in Applicants' patent US-A-4.548.918.

Some non-restrictive examples of organic solvents which may be used to prepare the catalyst are hydrocarbons, halogenated hydrocarbons, ketones and ethers. It is not essential to use a solvent when the tin, germanium and/or lead compound is itself liquid, as in the case e.g. of tetrabutyl tin.

Another method comprises working the moist carrier powder into the catalyst precursors then shaping and drying the mixture.

The following are some examples of metallic precursors which may be used to prepare the catalyst:

For the Group VIII metal, compounds such a chlorides, nitrates, halo-amino compounds, amino compounds and salts of organic acids which are soluble in the impregnating solvent may be used.

Organometallic compounds of a Group VIII metal in solution in an organic solvent may also be used, for example a hydrocarbon. Some examples of the hydrocarbons are saturated paraffin hydrocarbons where the hydrocarbon chain contains 6 to 12 carbon atoms per molecule, naphthene hydrocarbons containing 6 to 12 carbon atoms per molecule or aromatic hydrocarbons containing 6 to 2 carbon atoms per molecule. Some examples of organometallic compounds of the Group VIII metal are carbonyl and halocarbonyl compounds and acetyl acetonates, although the invention is not restricted to this list.

The element selected from the group made up of tin, germanium and lead may be introduced preferably in the form of at least one organic compound from the group formed by complexes, particularly polyketone complexes, of Group IVA metals and hydrocarbyl metals such as alkyl, cycloalkyl, aryl, alkylaryl and arylalkyl metals.

The IVA metal is advantageously introduced by means of a solution of the organometallic compound of the IVA metal in an organic solvent. Organohalogens of the IVA metals may equally be used. Some special examples of compounds of IVA metals are tetrabutyl tin, tetramethyl tin, tetrapropyl tin, tetrapropyl germanium, tetraethyl lead, diphenyl tin, diphenyl germanium and tetraphenyl lead.

The impregnating solvent is selected from the group comprising paraffin, naphthene or aromatic hydrocarbons containing 6 to 12 carbon atoms per molecule and halogenated organic compounds containing from 1 to 12 carbon atoms per molecule. Some examples are n-heptane, methylcyclohexane, toluene and chloroform. Mixtures of the above solvents may be used.

The element selected from the group comprising tin, germanium and lead may also be introduced by means of compounds such as tin chlorides, bromides and nitrate, lead halides, nitrates and acetate or germanium chloride and oxalate in aqueous or organic solution.

As already mentioned, the carrier may be of various types. A particularly well adapted carrier has specific characteristics such as a specific surface—determined by the BET method—of 10 to 500 m² per gram and preferably from 50 to 500 m2 per gram and a total pore volume of 0.2 to 1.3 cm3 per gram of carrier.

Once the metals have been fixed on the carrier the catalyst advantageously undergoes activation treatment in hydrogen at a high temperature, e.g. of 50°–600° C., to obtain an active metal phase. The procedure for this treatment in hydrogen may, for example, comprise slowly raising the temperature in a stream of hydrogen to the maximum reducing temperature, e.g. from 50° to 600° and preferably from 80° to 500°, then maintaining that temperature e.g. for 1 to 6 hours.

The following examples are non-restrictive and are given to illustrate the invention.

EXAMPLE 1 (COMPARATIVE)

The purpose is to reduce nitrobenzene.

The catalyst is prepared by impregnating a silica with a specific surface area of 280 m$^2$/g and a total pore volume of 80 cm$^3$/100 g with rhodium chloropentamine chloride in ammoniacal solution, followed by filtration, calcination in air at 450° C. and reduction in hydrogen at 450° C.

The final catalyst contains 1% of rhodium and will be called catalyst A.

Catalyst A is placed in a Grignard-type reactor containing an organic solvent, normal heptane. The reactor is then closed and purged of the air contained in it. The hydrogen pressure is increased to 40 bars (4 megapascal) and the temperature raised to 95° C. These conditions are maintained for 20 minutes.

The pressure and temperature are respectively brought down to 20 bars (2 megapascal) and 30° C. A solution of nitrobenzene in n-heptane is injected into the reactor in a ratio of 200 moles of nitrobenzene per gram atom of rhodium.

The evolution of the composition of the reaction medium is followed by gas phase chromatography.

The results obtained are set out in Table 1.

TABLE 1

| Time (h) | Conversion (%) | Selectivity (%) |
|---|---|---|
| 0 | 0 | — |
| 0.25 | 3 | 0 |
| 0.5 | 3 | 0 |
| 1.5 | 11 | 30 |
| 4 | 44 | 20 |
| 7.5 | 86 | 71 |
| 22 | 100 | 45 |

It will be seen that the maximum yield of aniline obtained under these conditions (conversion × selectivity) is 62%. Moreover no aniline is detected at the beginning of the reaction when part of the nitrobenzene is converted. Thus partially reduced reaction intermediates form, which have been identified by chromatography.

EXAMPLE 2 (ACCORDING TO THE INVENTION)

Catalyst A prepared in Example 1 is placed in a Grignard-type reactor containing an organic solvent, normal heptane. Tetrabutyl tin is injected into the solvent, and the reactor is closed and purged. The hydrogen pressure is increased to 40 bars (4 megapascal) and the temperature raised to 96° C. These conditions are maintained for 20 minutes with agitation.

The finished catalyst has an atomic tin:rhodium ratio of 2 and will be called catalyst B; percentage of Rh: 1% (wt), percentage of Sn: 2.2% (wt).

The pressure and temperature are respectively brought down to 20 bars (2 megapascal) and 30° C. A solution of nitrobenzene in n-heptane is injected into the reactor in a ratio of 200 moles of nitrobenzene per gram atom of rhodium. Thus one is working under the same conditions as in Example 1.

The evolution of the composition of the reaction medium is followed by gas phase chromatography.

The results obtained are set out in Table 2.

TABLE 2

| Time (h) | Conversion (%) | Selectivity (%) |
|---|---|---|
| 0 | 0 | — |
| 1 | 44 | 91 |
| 1.5 | 87 | 82 |
| 2 | 97 | 100 |
| 3 | 97 | 98 |
| 20 | 97 | 84 |

The maximum yield of aniline in the presence of catalyst B is 97%. This time the disappearance of the nitrobenzene in the medium corresponds to the formation of aniline. No partially reduced reaction intermediates are detected, the only compound present in the medium with the aniline being traces of cyclohexylamine.

The time required for 85% conversion of nitrobenzene is found to be five times shorter with this catalyst B than with catalyst A.

EXAMPLE 3 (COMPARATIVE)

Here the aim is to reduce 1-chloro 4-nitrobenzene.

Catalyst A prepared in Example 1 is placed in a Grignard-type reactor containing an organic solvent, normal heptane. The reactor is then closed and purged. The hydrogen pressure is increased to 40 bars (4 megapascal) and the temperature raised to 96.C. These conditions ar maintained for 20 minutes with agitation.

The pressure and temperature are respectively brought down to 20 bars (2 megapascal) and 30° C. A solution of 1-chloro 4-nitrobenzene in n-heptane is injected into the reactor in a ratio of 200 moles of 1-chloro 4-nitrobenzene per gram atom of rhodium.

The evolution of the composition of the reaction medium is followed by gas Phase chromatography.

The results obtained are set out in Table 3.

TABLE 3

| Time (h) | Conversion (%) | Selectivity (%) |
|---|---|---|
| 0 | 0 | — |
| 0.5 | 7 | 0 |
| 1 | 10 | 0 |
| 1.5 | 14 | 0 |
| 3 | 26 | 0 |
| 4 | 38 | 6 |
| 20 | 100 | 21 |

The yield of 1-chloro 4-aminobenzene obtained is 21% after 20 hours. Thus there is significant dechlorination of the substrate during the reaction.

EXAMPLE 4 (ACCORDING TO THE INVENTION)

Catalyst A prepared in Example 1 is placed in a Grignard-type reactor containing an organic solvent, normal heptane. Tetrabutyl tin is injected into the solvent, and the reactor is closed and purged. The hydrogen pressure is increased to 40 bars (4 megapascal) and the temperature raised to 96° C. These conditions are maintained for 20 minutes with agitation.

The finished catalyst has an atomic tin:rhodium ratio of 2; percentage of Rh: 1%(wt), percentage of Sn: 2.2%(wt).

The pressure and temperature are respectively brought down to 20 bars (2 megapascal) and 30° C. A solution of 1-chloro 4-nitrobenzene in n-heptane is injected into the reactor in a ratio of 200 moles of 1-chloro 4-nitrobenzene per gram atom of rhodium, as in Example 3.

The evolution of the composition of the reaction medium is followed by gas phase chromatography.

The results obtained are set out in Table 4.

TABLE 4

| Time (h) | Conversion (%) | Selectivity (%) |
|---|---|---|
| 0 | 0 | — |
| 0.5 | 34 | 13 |
| 1.5 | 82 | 88 |
| 3 | 100 | 99.7 |
| 4 | 100 | 97 |
| 20 | 100 | 64 |

The maximum yield of 1-chloro 4-aminobenzene obtained is 99.7% after 3 hours. There is thus very little dechlorination of the substrate. On the other hand the time taken to convert 38% of the 1-chloro 4-nitrobenzene is seven times shorter than in Example 3.

EXAMPLE 5 (ACCORDING TO THE INVENTION)

Reduction of 1-chloro 2-nitrobenzene.

Catalyst A prepared in Example 1 is placed in a Grignard-type reactor containing an organic solvent, normal heptane. Tetrabutyl tin is injected into the solvent, and the reactor is closed and purged. The hydrogen pressure is increased to 40 bars (4 megapascal) and the temperature raised to 96° C. These conditions are maintained for 20 minutes with agitation.

The finished catalyst has an atomic tin:rhodium ratio of 2 ; percentage of Rh: 1% (wt), percentage of Sn: 2.2% (wt).

The pressure and temperature are respectively brought down to 20 bars (2 megapascal) and 30° C. A solution of 1-chloro 2-nitrobenzene in n-heptane is injected into the reactor in a ratio of 200 moles of 1-chloro 2-nitrobenzene per gram atom of rhodium.

The evolution of the composition of the reaction medium is followed by gas phase chromatography.

The results obtained are set out in Table 5.

TABLE 5

| Time (h) | Conversion (%) | Selectivity (%) |
|---|---|---|
| 0 | 0 | — |
| 1 | 7 | 57 |
| 1.5 | 11 | 67 |
| 2 | 19 | 66 |
| 2.5 | 22 | 84 |
| 3 | 26 | 100 |
| 4 | 39 | 100 |
| 20 | 98 | 100 |

The maximum yield of 1-chloro 2-aminobenzene obtained in this example is 98%. The tendency to inhibit dechlorination in the presence of catalyst B, observed in Example 4, is confirmed here with the total absence of dechlorination.

We claim:

1. A method of producing an aminoaromatic compound of one of the formulae (III) or (IV)

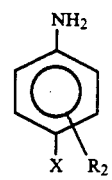

(III)

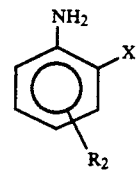

(IV)

where X is a halogen and $R_2$ is hydrogen, alkyl, halogen, alkenyl, sulphoxy, amino, hydroxyl, ethoxy or acetoxy group, by selective hydrogenation in the presence of hydrogen of at least one nitro group on the aromatic ring of a nitroaromatic compound of formula (I) or (II)

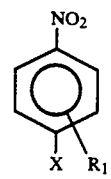

(I)

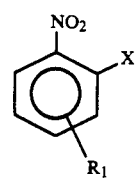

(II)

where X is a halogen and $R_1$ is hydrogen, alkyl, halogen, alkenyl, sulphoxy, nitro, nitroso, amino, hydroxyl, ethoxy or acetoxy group, wherein the hydrogenation is effected in the presence of a catalyst containing a carrier and further containing:
 (a) at least one Group VIII metal selected from the group consisting of rhodium, ruthenium and mixtures thereof; and
 (b) at least one additional Group IVA metal element selected from the group consisting of tin, germanium and mixtures thereof.

2. The method of claim 1, wherein the weight percentage of Group VIII metal relative to the total mass of catalyst is from 0.1 to 10%.

3. The method of claim 2, wherein said percentage is from 0.5 to 5%.

4. The method of claim 1, wherein the weight percentage of Group IVA metal relative to the total mass of catalyst is from 0.01 to 10%.

5. The method of claim 4, wherein said percentage is from 0.1 to 5%.

6. The method of claim 1, wherein the the molar ratio of Group IV metal element to Group VIII metal is from 0.8 to 3:1.

7. The method of claim 6, wherein said ratio is from 0.9 to 2.6:1.

8. The method of claim 1, wherein the catalyst contains at least two Group IVA metals.

9. The method of claim 1 wherein the Group VIII metal is rhodium.

10. The method of claim 1 wherein the Group VIII metal is ruthenium.

11. The method of claim 1 wherein the Group IVA metal is germanium.

12. The method of claim 1 wherein the Group IVA metal is tin.

* * * * *